United States Patent [19]

Kawamoto et al.

[11] 4,425,277

[45] Jan. 10, 1984

[54] METHOD FOR THE PREPARATION OF ALKENYL ESTERS OF CARBOXYLIC ACIDS

[75] Inventors: Fumiaki Kawamoto, Sakai; Shozo Tanaka, Osaka; Yoshihiro Honma, Sakai, all of Japan

[73] Assignee: Shin-Etsu Vinyl Acetate Co., Ltd., Japan

[21] Appl. No.: 62,133

[22] Filed: Jul. 30, 1979

Related U.S. Application Data

[63] Continuation-in-part of Ser. No. 928,710, Jul. 27, 1978, abandoned.

[30] Foreign Application Priority Data

Oct. 13, 1977 [JP] Japan .............................. 52-122882
Dec. 26, 1977 [JP] Japan .............................. 52-156928

[51] Int. Cl.$^3$ .......................... C07C 67/10; C11C 3/10
[52] U.S. Cl. .............................. 260/410.9 N; 260/408; 560/100; 560/104; 560/113; 560/217; 560/226; 560/234; 502/170; 502/174; 502/180; 502/201; 502/230; 502/245
[58] Field of Search .............. 560/217, 113, 234, 104, 560/226, 100; 252/429 R; 260/405.5, 410.9 N, 408

[56] References Cited

U.S. PATENT DOCUMENTS

| | | | |
|---|---|---|---|
| 3,188,319 | 6/1965 | Smidt et al. | 560/217 |
| 3,190,912 | 6/1965 | Robinson | 560/113 |
| 3,624,141 | 11/1971 | Copelin | 252/429 R |
| 3,755,387 | 8/1973 | Young | 560/217 |

OTHER PUBLICATIONS

Smidt, J. et al., Angewandte Chemie, vol. 74, pp. 93–101, (1962).
Smidt, J., Chemistry & Industry, (London) pp. 54–61, (1962).
Sabel, A., Chemisches Berichte, vol. 102, pp. 2939–2949, (1969).

*Primary Examiner*—Natalie Trousof
*Assistant Examiner*—L. Hendriksen
*Attorney, Agent, or Firm*—McGlew and Tuttle

[57] ABSTRACT

A novel and effective catalyst system is provided for application in the preparation of alkenyl esters of carboxylic acids by transesterification reaction. The catalyst system consists of a palladium compound as the main ingredient and a cocatalyst formed of an alkali metal compound and a copper compound, at least one of which is a halide. The catalyst ingredients are adsorbed on a solid catalyst carrier, so that repeated use of the combined catalyst or a continuous operation of the reaction can easily be facilitated.

4 Claims, No Drawings

METHOD FOR THE PREPARATION OF ALKENYL ESTERS OF CARBOXYLIC ACIDS

BACKGROUND OF THE INVENTION

This application is a continuation-in-part of our co-pending application bearing Ser. No. 928,710 and filed on July 27, 1978, now abandoned.

The present invention relates to an improved method for the preparation of alkenyl esters of carboxylic acids by transesterification or ester interchange.

Several methods are known for the preparation of alkenyl esters of carboxylic acids, in particular, vinyl esters of carboxylic acids, by transesterification. According to an example of the prior art methods, a vinyl ester and an aliphatic or aromatic carboxylic acid are subjected to transesterification reaction in the presence of a mercury salt as the catalyst, such as, mercury(II) sulfate and mercury(II) acetate, to produce a vinyl ester which is different from the starting vinyl ester. This method is not recommendable for the reason that the mercury compounds used are noxious.

According to another example of the prior art methods, the catalyst used is a combination of palladium acetate with a chelating agent, such as, bipyridil or 1,10-phenanthroline (see TETRAHEDRON, vol. 28, 1972, page 233). This method has the disadvantages that the chelate compound of palladium as the catalyst should be formulated separately and inconveniently before it is actually applied to the transesterification reaction and, in addition, that the chelating agents are so expensive that the cost of the final product will inevitably be higher.

Further, when the above-mentioned palladium acetate is used in the "unchelated" form or in combination with an acetate of alkali metals, e.g. sodium acetate, the transesterification reaction is discontinued as the palladium acetate is rapidly decomposed into metallic palladium in the course of the reaction (see Canadian Journal of Chemistry, vol. 53, 1975, page (2223). In this case, the metallic palladium thus formed may be recovered and recycled, resulting in compensating for the expensiveness of palladium acetate, but it may be pointed out that such recovery and recycling processes have difficulties in operation.

Furthermore, palladium chloride or a double chloride of palladium and an alkali metal has been proposed as the catalyst. (see U.S. Pat. No. 3,188,319). A problem in the use of this catalyst is that a relatively large amount of palladium salt is required to obtain a satisfactorily high reaction velocity and that the palladium salt is expensive, bringing about an increased cost of production.

SUMMARY OF THE INVENTION

It is therefore an object of the present invention to provide an improved method free from the above-described disadvantages encountered in the prior art for the preparation of an alkenyl ester of a carboxylic acid by subjecting an alkenyl ester different from the alkenyl ester as the desired product to transesterification with the corresponding carboxylic acid.

In accordance with the method of the present invention, an alkenyl ester of a carboxylic acid represented by the general formula $$R^1COOR^3 \tag{I}$$

where $R^1$ is a hydrogen atom or a substituted or unsubstituted aliphatic or aromatic monovalent hydrocarbon group and $R^3$ is an alkenyl group can be prepared by subjecting to a liquid-phase reaction of transesterification a carboxylic acid represented by the general formula $$R^1COOH \tag{II}$$

where $R^1$ is the same as defined above and an ester compound represented by the general formula $$R^2COOR^3 \tag{III}$$

where $R^2$ is a hydrogen atom or a substituted or unsubstituted monovalent hydrocarbon group which is different from $R^1$ above and $R^3$ is the same as defined above, in the presence of a main catalyst of a palladium compound and a cocatalyst consisting of a combination of an alkali metal compound and a copper(II) compound, at least one of which is a halide, preferably a bromide, the amount of the copper(II) compound being from about 0.001 to about 1.0 part by weight and the amount of the alkali metal compound being from about 1 to 15 parts by weight, all per 100 parts by weight of the total amount of the carboxylic acid and the ester compound, and the weight ratio of the copper(II) compound to the alkali metal compound being, preferably, in the range from 0.001 to 0.5.

The reaction in this case is conducted preferably in an oxidizing atmosphere containing oxygen, such as air. According to the method, the problem of decomposition of the palladium compound encountered in the prior art methods can almost completely be eliminated, and the catalysts can be used repeatedly without the troublesome recovery of metallic palladium. The catalyst ingredients may be used as adsorbed on a solid catalyst carrier, so that the reaction is performed by a heterogeneous phase catalysis and, hence, repeated use of the catalysts can be still more simplified.

DETAILED DESCRIPTION OF THE PREFERRED EMBODIMENTS

In the above-mentioned formula (II) representing the aliphatic or aromatic carboxylic acids as one of the starting reactants, $R^1$ is a hydrogen atom or a substituted or unsubstituted aliphatic or aromatic monovalent hydrocarbon group exemplified by alkyl groups, such as methyl, ethyl, propyl, butyl, undecyl, heptadecyl and octadecyl groups; alkenyl groups, such as vinyl and allyl groups; aryl groups, such as phenyl and naphthyl groups; and those groups with substituent or substituents, such as halogen atoms, in place of part or all of the hydrogen atoms in the above-named hydrocarbon groups.

The carboxylic acids suitable for use in the method of the present invention are, for example, aliphatic saturated carboxylic acids, such as formic acid, propionic acid, butyric acid, lauric acid, and stearic acid; unsaturated carboxylic acids, such as acrylic acid, methacrylic acid, and crotonic acid; aromatic carboxylic acids, such as benzoic acid and cinnamic acid; and their derivatives, e.g. halogen derivatives, such as monochloroacetic acid.

The alkenyl ester compounds as the other starting reactant useful in the method is represented by formula (III) above, where $R^2$ is a hydrogen atom or a substituted or unsubstituted monovalent hydrocarbon group similar to those of group $R^1$ as described above provided naturally that groups $R^1$ and $R^2$ must not be the same, while $R^3$ is an alkenyl group, such as vinyl group and allyl group.

The alkenyl esters of carboxylic acids according to the present invention are exemplified by vinyl formate, vinyl acetate, vinyl butyrate, vinyl cyclopropanecarboxylate, isopropenyl acetate, and allyl acetate.

The method of the present invention is applicable, for example, to the preparation of the following. Allyl acrylate from acrylic acid and allyl acetate; vinyl acrylate from acrylic acid and vinyl acetate; isopropenyl acrylate from acrylic acid and isopropenyl acetate; vinyl methacrylate from methacrylic acid and vinyl acetate; vinyl crotonate from crotonic acid and vinyl acetate; vinyl propionate from propionic acid and vinyl acetate; vinyl monochloroacetate from monochloroacetic acid and vinyl acetate; vinyl cinnamate from cinnamic acid and vinyl acetate; and vinyl benzoate from benzoic acid and vinyl acetate.

The molar ratio of the carboxylic acid and the alkenyl ester compound as the starting reactants generally ranges between 20:80 and 80:20, and should be determined in consideration of the equilibrium to be established in the transesterification reaction;

$$R^1COOH + R^2COOR^3 \rightleftarrows R^1COOR^3 + R^2COOH$$

The palladium compounds as the main ingredient of the catalyst system suitable for the purpose are exemplified by carboxylates of palladium, such as palladium acetate and palladium propionate, and inorganic salts of palladium, such as palladium chloride, palladium bromide, and palladium nitrate.

The cocatalyst used with the above palladium compound is a combination of an alkali metal compound and a copper(II) compound, at least one of which is a halide, preferably a bromide. The alkali metal compounds suitable for the purpose are exemplified by inorganic and organic salts of alkali metals, such as sodium carbonate, potassium acetate, sodium chloride, sodium bromide, potassium iodide, and potassium bromide; and hydroxide of alkali metals, such as sodium hydroxide and potassium hydroxide. The copper(II) compounds are exemplified by copper(II) acetate, copper(II) nitrate, copper(II) oxide, copper(II) chloride, and copper(II) bromide. The combination of the alkali metal and the copper(II) compounds as the cocatalyst should include at least one halogen compound selected from the alkali metal halides, such as sodium chloride, sodium bromide, potassium iodide, and potassium bromide and the copper(II) halides, such as copper(II) chloride, copper(II) bromide, and copper(II) iodide.

The individual catalyst ingredients are usually composed of from 0.001 to 0.5 part by weight of the palladium compound, from 1 to 15 parts by weight of the alkali metal compound and from 0.001 to 1.0 part by weight of the copper(II) compound, each per 100 parts by weight of the total amount of the carboxylic acid and the alkenyl ester compound as the starting reactants. The weight ratio of the copper(II) compound to the alkali metal compound is, preferably, in the range from 0.001 to 0.5. The amounts of the catalyst ingredients are not narrowly critical, and may be appropriately determined according to various factors. It is of course optional that compounds of alkali metals or copper other than halides can be used in combination with the alkali metal halides or copper(II) halides, respectively. The amount of the halide either of an alkali metal or of copper is, desirably, at least 0.01 part by weight per 100 parts by weight of the total amount of the starting reactants. It should be noted that since the alkali metal compound has a limited solubility in the reaction mixture, its use in amounts exceeding the above-given range does not necessarily contribute to any more remarkable effects.

The transesterification reaction according to the present invention is carried out by use of the combined catalyst system of a palladium compound and a cocatalyst composed of an alkali metal compound and a copper(II) compound including at least one halide. In the reaction, the atmosphere contacting the surface of the reaction mixture is preferably oxygen or an oxygen-containing gas, such as air, rather than an inert gas like nitrogen, so that better results may be obtained in the preservation of the catalytic activity. If necessary, the pressure of the atmosphere may be increased to a superatmospheric pressure.

According to the improved method of the present invention using the catalyst system, the palladium compound as the main catalytic ingredient no longer permits reduction to metallic palladium or deactivation in the course of the transesterification reaction, and its catalytic activities can be preserved to be suited for use in repeated runs of the reaction. The copper(II) and the alkali metal compounds as the cocatalyst retain their activities and can be employed repeatedly in the form as such. Thus, a residue remaining after the reaction mixture is distilled following completion of the reaction still has catalytic activities so high enough that its mixture with fresh portions of the starting reactants can exhibit a reaction as satisfactorily as a similar mixture with fresh catalyst ingredients instead of the residue, and may be used repeatedly in several successive runs of the reaction.

Further according to the discovery of the inventors, the recycling of the catalyst for repeated use can be more facilitated when the catalyst ingredients are employed as adsorbed on a solid catalyst carrier, such as silica gel, not as dissolved in the reaction mixture. When the catalyst is employed as dissolved in the reaction mixture effecting homogeneous catalysis, it has to be separated from the reaction mixture as a residue by distillation. On the other hand, the solid catalyst effecting heterogeneous catalysis can readily be separated from the reaction mixture by simple decantation, filtration, centrifugal separation or other conventional solid-liquid separation techniques, by which the recycling of the catalyst is much simplified and the loss of the expensive palladium compound during the process of recovering without affecting the catalytic activities or, consequently, the reaction velocity can be avoided.

The catalyst ingredients to be adsorbed on the solid catalyst carrier may be either the palladium compound as the main ingredient alone or both the palladium compound and the cocatalyst.

The carriers on which the catalyst ingredients are adsorbed are exemplified by active carbon, silica gel, and silica-alumina gel, among which active carbon is most preferred.

The solid catalyst may be prepared in accordance with the conventional liquid phase method. Namely, the catalyst carrier is dipped in a solution of the catalyst ingredients dissolved in a suitable solvent to have the catalyst ingredients adsorbed on its surface, and the resulting carrier is separated from the solution and then dried, if necessary, with heat to produce the desired solid catalyst bearing the catalyst ingredients on the surface.

Illustrative of the solvents suitable for use in the preparation of the solid catalyst are hydrochloric acid, acetic acid, benzene and the like. The carboxylic acid which is one of the starting reactants may be used as the solvent. In this case, the catalyst carrier is immersed in the carboxylic acid containing the palladium compound for a length of time sufficient to establish an adsorption equilibrium, and then direct to this solution are added the alkenyl ester which is the other starting reactant and the cocatalyst ingredients, to allow the contents to the desired reaction.

The palladium compounds to be adsorbed on the catalyst carrier are exemplified by carboxylates of palladium, such as palladium acetate and palladium propionate; inorganic salts of palladium, such as palladium chloride, palladium bromide, and palladium nitrate; and complex compounds of palladium, such as dichlorobis(benzonitrile)palladium. The amount of the palladium compound adsorbed on the carrier is preferably in the range from 1 to 10 parts by weight as palladium per 100 parts by weight of the catalyst carrier, though not limitative but adjustable according to need. The palladium compound adsorbed on the carrier may be reduced to metallic palladium by suitable means, for example, dipping the carrier in an aqueous solution of potassium hydroxide and formaldehyde.

The cocatalyst ingredients to be used in combination with the palladium catalyst are an alkali metal compound and a copper(II) compound in combination, at least one of which is a halide, preferably, a bromide. The alkali metal compounds are exemplified by inorganic and organic salts of alkali metals, such as sodium carbonate, sodium acetate, sodium chloride, sodium bromide, potassium iodide, and potassium bromide; and alkali metal hydroxides, such as sodium hydroxide and potassium hydroxide. The copper(II) compounds are exemplified by copper(II) acetate, copper(II) oxide, copper(II) chloride, and copper(II) bromide. Further, illustrative of the halides are sodium chloride, sodium bromide, potassium iodide, potassium bromide, copper(II) chloride, copper(II) bromide and the like.

With respect to the amounts of the individual catalyst ingredients, the cocatalyst being used in the homogeneous phase, an example may be from about 0.001 to about 0.5 part by weight of the palladium compound; from about 1 to 15 parts by weight of the alkali metal compound; or from about 0.001 to about 1.0 part by weight of the copper(II) compound, all per 100 parts by weight of the total amount of the carboxylic acid and the alkenyl ester as the starting reactants. These ranges are not narrowly limitative and may be adjusted appropriately according to requirements. It is optional in this case to use compounds of alkali metals or copper other than halides in combination with the halides, but it is recommended that the amount of the halide is at least 0.001 part by weight per 100 parts by weight of the starting reactants.

As is described above, either the copper(II) compound or the alkali metal compound is desirably a halide or, preferably, a bromide. When an alkali metal bromide, e.g. potassium bromide, is used as the bromide, however, the potassium bromide should be used as combined with a more soluble alkali metal compound, e.g. potassium acetate, since the solubility of potassium bromide in the reaction mixture is rather limited. Thus, it is recommended that the amount of the alkali metal bromide is limited to range between 0.001 and 0.5 part by weight per 100 parts by weight of the total amount of the carboxylic acid and the ester compound.

The transesterification reaction with the palladium-bearing solid catalyst according to the present invention is usually carried out at room temperature or higher.

According to another embodiment of the invention, the cocatalyst is adsorbed on the solid catalyst carrier simultaneously with the palladium compound as the main ingredient of the catalyst system. In this case, the palladium compounds are the same as previously shown, while the cocatalyst is an alkali metal halide, a copper(II) halide or a combination of an alkali metal compound and a copper(II) compound, at least one of which is a halide. Among the halides, the most preferred are bromides. When the palladium compound is palladium bromide, the cocatalyst may not always include a halide.

The solid catalyst composed of both the palladium compound and the cocatalyst as adsorbed on a carrier may be prepared by dipping the carrier in a solution containing both the palladium compound and the cocatalyst ingredients, taking the resulting carrier out of the solution, and then drying it. Alternatively, the dipping process is carried out first in a solution containing the palladium compound and then in a separate solution containing the cocatalyst ingredients. The solvent to be used is hydrochloric acid, acetic acid, benzene or the like, but water is recommended for forming the solution containing the cocatalyst ingredients alone.

With respect of the individual catalyst ingredients to be adsorbed on the catalyst carrier, they are from 1 to 10 parts by weight of the palladium compound as palladium and 0.1 to 10 times in moles of the halide as the cocatalyst ingredient per 100 parts by weight of the solid catalyst carrier, though not limitative. Further, the amounts of the catalyst ingredients relative to the amounts of the reactants are from 0.001 to 0.5 part by weight of the palladium compound, from 1 to 15 parts by weight of the alkali metal compound and from 0.001 to 1 part by weight of the copper(II) compound, all per 100 parts by weight of the total amount of the carboxylic acid and the alkenyl ester as the starting reactants. When the cocatalyst is a combination of a halide of an alkali metal or copper with one or more of the compounds of these elements other than halides, it is desirable that the amount of the halide is at least 0.001 part by weight. The reaction temperature is room temperature or higher.

The transesterification reaction with the solid catalyst is performed either by suspending the solid catalyst in the reaction mixture of the carboxylic acid and the alkenyl ester, optionally, diluted with a solvent, such as tetrahydrofuran and acetonitrile, under agitation or passing the reaction mixture to a fixed bed of the solid catalyst in a reaction column. It is natural that the reaction mixture contains the cocatalyst ingredients when the active ingredient on the solid catalyst is the palladium compound alone. It is optional that the reaction mixture is admixed with the cocatalyst ingredients even when the solid catalyst bears the cocatalyst ingredients in addition to the palladium compound. The copper(II) compound adsorbed on the solid catalyst carrier is partly reduced to lower oxidation state in the course of the reaction. The copper compound in a lower oxidation state is readily re-oxidized into the active form of the copper(II) compound by being contacted with oxygen or air after the reaction or by keeping the reaction mixture in good contact with oxygen or air throughout the reaction, so that the solid catalyst can maintain lasting catalytic activities.

The following examples are to illustrate the method of the present invention in further detail but not to limit the scope of the invention.

EXAMPLE 1

Into a 200-ml flask equipped with a stirrer, a thermometer and a cooling tube were introduced 74 g of propionic acid, 86 g of vinyl acetate, 44.8 mg of palladium acetate, 9.8 g of potassium acetate, 36.4 mg of copper(II) acetate, and 47.6 mg of potassium bromide. The mixture was heated at 60° C. for 48 hours with agitation to bring the surface of the mixture in good contact with air to effect transesterification. The yield of the desired vinyl propionate was 30.0 g, while 18.0 g of acetic acid was recovered as a by-product.

Throughout the course of the reaction, the reaction mixture remained transparent in blue with no precipitation of palladium black.

The same experimental procedure was repeated as above except the ommission of potassium bromide and, as a result, the yield of vinyl propionate was 5.0 g with 3.0 g of acetic acid removed as a by-product.

EXAMPLE 2

The same experimental procedure as in Example 1 above was repeated except 44.7 mg of copper(II) bromide was employed instead of copper(II) acetate and potassium bromide. The yield of vinyl propionate was 29.0 g, with 17.4 g of acetic acid recovered as a by-product.

Throughout the course of the reaction, the reaction mixture remained transparent in blue with no precipitation of palladium black.

The results of this example when compared with those of Example 1 clearly indicate a copper(II) halide having an equivalency with respect to its catalytic activity to the combustion of a copper(II) compound other than halide and an alkali metal halide.

EXAMPLE 3

Into the same flask as employed in Example 1 were introduced 37 g of propionic acid, 43 g of vinyl acetate, 44.8 mg of palladium acetate, 71.5 mg of copper(II) bromide, and 980 mg of potassium acetate. The mixture was heated at 60° C. for 20 hours with agitation to ensure good contact of its surface with air. The yield of the desired vinyl propionate was 24.9 g, while 14.9 g of acetic acid was recovered as a by-product.

The reaction mixture remained transparent in green with no precipitation of palladium black.

The above reaction mixture was subjected to distillation under reduced pressure to produce 3.05 g of a residue. Using this residue and adding thereto 34.93 g of propionic acid and 43 g of vinyl acetate, another reaction was conducted in the same manner and, as a result, 25.0 g of the desired vinyl propionate was obtained, and 15.0 g of acetic acid was recovered as a by-product.

The reaction mixture was also transparent in green without precipitation of palladium black.

When the same experimental procedure as in the above first reaction was performed with the exception of the omission of copper(II) bromide, the yield of vinyl propionate was 12.0 g with 7.2 g of acetic acid recovered as a by-product. In this case, the reaction mixture was brown with precipitation of palladium black. Further, 33.98 g of propionic acid and 43 g of vinyl acetate were admixed with the residue obtained by the distillation of the above reaction mixture, followed by similar heating to effect the reaction, resulting in forming no vinyl propionate.

EXAMPLE 4

Into a 500-ml flask equipped with a stirrer, a thermometer and a cooling tube were introduced 148 g of propionic acid, 172 g of vinyl acetate, 44.8 mg of palladium acetate, 71.5 mg of copper(II) bromide and 3.92 g of potassium acetate. The reaction mixture was heated at 60° C. for 72 hours with agitation to ensure good contact of its surface with air. The yield of the desired vinyl propionate was 96.0 g with 57.6 g of acetic acid recovered as a by-product.

The reaction mixture was transparent in green without precipitation of palladium black.

When the same experimental procedure as above was repeated except that the air inside the flask was replaced with nitrogen gas, the yield of vinyl propionate was 73.2 g with 44.0 g of acetic acid recovered as a by-product. The reaction mixture in this case was pale-orange with precipitation of palladium black, indicating the deactivation of the catalyst.

EXAMPLE 5

Into the same flask as employed in Example 1 were introduced 36 g of acrylic acid, 43 g of vinyl acetate, 44.8 mg of palladium acetate, 89.4 mg of copper(II) bromide and 4.9 g of potassium acetate. The reaction mixture was heated at 40° C. for 20 hours with agitation to ensure good contact of its surface with air. The yield of the desired vinyl acrylate was 16.3 g with 10.0 g of acetic acid recovered as a by-product.

The reaction mixture was transparent in green with precipitation of a very small amount of palladium black.

When the same experimental procedure as above was repeated with the exception that the air inside the flask was replaced with nitrogen gas, the yield of vinyl acrylate was only 2.6 g, and the reaction mixture was brown with precipitation of palladium black, indicating the deactivation of the catalyst.

Further the same experimental procedure was repeated with the omission of copper(II) bromide. The yield of vinyl acrylate was only 2.5 g. The reaction mixture was brown with the precipitation of palladium black, indicating the deactivation of the catalyst.

EXAMPLE 6

Into the same flask as employed in Example 4 were introduced 24.4 g of benzoic acid, 120.4 g of vinyl acetate, 11.2 mg of palladium acetate, 44.7 mg of copper(II) bromide, 1.96 g of potassium acetate and 50 ml of acetonitrile and 50 ml of tetrahydrofuran as the solvents. The reaction mixture was heated at 60° C. for 72 hours with agitation to ensure good contact of its surface with air. The yield of the desired vinyl benzoate was 22.4 g with 10.0 g of acetic acid recovered as a by-product.

The reaction mixture was transparent in pale-green without precipitation of palladium black.

When the same experimental procedure as above was repeated except that the air inside the flask was replaced with nitrogen gas, the yield of vinyl benzoate was 16.6 g with 6.7 g of acetic acid as a by-product. In this case, the reaction mixture was pale-orange with precipitation of palladium black, indicating the deactivation of the catalyst.

In comparison, the same experimental procedure was repeated with the omission of copper(II) bromide, which resulted in the formation of only 3.8 g of vinyl benzoate. In this case, the reaction mixture was turbid in greyish white with precipitation of palladium black, indicating the deactivation of the catalyst.

In further comparison, potassium acetate was omitted from the catalyst system and the reaction was conducted in the same manner with the other conditions unchanged. In this case, the yield of vinyl benzoate was 9.0 g with 3.6 g of acetic acid recovered as a by-product, although the reaction mixture remained transparent in green throughout the reaction.

EXAMPLE 7

Into the same flask as employed in Example 4 were introduced 56.9 g of stearic acid, 120.4 g of vinyl acetate, 11.2 mg of palladium acetate, 44.7 mg of copper(II) bromide, 1.96 g of potassium acetate and 50 ml of acetonitrile and 50 ml of tetrahydrofuran as the solvents. The reaction mixture was heated at 60° C. for 72 hours with agitation to ensure good contact of its surface with air. The yield of the desired vinyl stearate was 43.4 g with 8.4 g of acetic acid recovered as a by-product.

The reaction mixture was transparent in bluish green without precipitation of palladium black.

Ths same experimental procedure as above carried out in an atmosphere of nitrogen gas instead of air resulted in yielding 34.1 g of vinyl stearate with 6.6 g of acetic acid recovered as a by-product. The same reaction mixture after the reaction was pale-orange with precipitation of palladium black, indicating deactivation of the catalyst.

In comparison, the same experimental procedure was repeated excepting the omission of copper(II) bromide from the catalyst system to give 8.9 g of vinyl stearate with 1.7 g of acetic acid recovered as a by-product. The reaction mixture after the reaction was turbid in greyish white with precipitation of palladium black, indicating deactivation of the catalyst.

In further comparison, potassium acetate was omitted from the catalyst system and the reaction was undertaken with the other conditions unchanged, to produce 8.9 g of vinyl stearate with 1.7 g of acetic acid recovered as a by-product, the reaction mixture remaining transparent in green.

EXAMPLE 8

Into a 2-liter autoclave were introduced 360 g of acrylic acid, 430 g of vinyl acetate, 448 mg of palladium acetate, 2.233 g of copper(II) bromide and 49 g of potassium acetate. Air inside the autoclave was replaced with oxygen, to have a pressure of 10 atmospheres. Then the contents of the autoclave was heated at 60° C. for 6 hours with agitation to effect transesterification, resulting in the formation of 210.7 g of vinyl acrylate with 129.0 g of acetic acid recovered as a by-product.

The reaction mixture after completion of the reaction was transparent in green with no precipitation of palladium black.

In comparison, the same experimental procedure as above was repeated excepting the omission of copper(II) bromide, to produce only 53.9 g of vinyl acrylate with 33.0 g of acetic acid recovered as a by-product. The reaction mixture after completion of the reaction in this case was brown with precipitation of palladium black, indicating complete deactivation of the catalyst.

EXAMPLE 9

Granular active carbon of 16 to 32 mesh particle size weighing 10 g was placed in a solution of 600 mg of palladium chloride in 50 ml of 9 N hydrochloric acid, and allowed to stand at 40° C. for 12 hours. Thereupon, the material was filtered and dried at room temperature in a vacuum desiccator, to finally form a palladium-bearing solid catalyst, about 98% of palladium chloride having been adsorbed on the active carbon.

1.34 g of the solid catalyst thus formed was put into a 300-ml flask which was equipped with a stirrer, a thermometer and a cooling tube, together with a mixture consisting of 74 g of propionic acid, 86 g of vinyl acetate, 9.8 g of potassium acetate, 67 mg of copper(II) bromide and 127 mg of copper(II) acetate. The resulting mixture was heated at 60° C. for 12 hours with agitation so that its surface could well contact with air. As a result, 45.0 g of the desired vinyl propionate was formed, while 27.0 g of acetic acid was recovered as the by-product.

The solid catalyst was then separated from the reaction mixture by decantation and thereto was added a fresh portion of the same mixture in the same amount as above-mentioned, followed by reaction under the same conditions and for the same period of time as above. As a result, 44.5 g of vinyl propionate was formed, while 26.7 g of acetic acid was recovered as the byproduct.

The above series of experiments evidently demonstrate that the solid catalyst is advantaged by easy separation from the reaction mixture and also by being able to be recycled to following runs of reaction with very little decreasing catalytic activities.

EXAMPLE 10

Granular active carbon of 16 to 32-mesh particle size weighing 10 g was placed in a solution of 760 mg of palladium acetate in 65 ml of propionic acid, and allowed to stand at room temperature for 12 hours. Thereupon, the material was filtered and dried at room temperature in a vacuum desiccator, to finally form a palladium-bearing solid catalyst, about 48% of palladium acetate having been adsorbed on the active carbon.

Then the same experimental procedure as in Example 9 followed using 1.39 g of the above solid catalyst under the same conditions for 24 hours. As a result, 46.5 g of vinyl propionate was formed, while 27.9 g of acetic acid was recovered as the byproduct.

EXAMPLE 11

Granular alumina gel of 4 to 8-mesh particle size (Neobead C, product of Mizusawa Chemical Co., Japan) weighing 15 g was placed in a solution of 325 mg of dichlorobis(benzonitrile)palladium in 30 ml of benzene, and allowed to stand at room temperature for 12 hours. Thereupon, the material was filtered and dried at room temperature in a vacuum desiccator, about 98% of the palladium compound having been adsorbed on the alumina.

Then the same experimental procedure as in Example 9 followed using 1.65 g of the above palladium-bearing alumina catalyst instead of the palladium-bearing carbon catalyst under the same conditions for 12 hours. As a result, 45.9 g of vinyl propionate was formed, while 27.5 g of acetic acid was recovered as the byproduct.

EXAMPLE 12

A U-shaped glass tube of 8 mm in inside diameter filled with 15 ml of the solid catalyst prepared in Example 9 was kept at 60° C. in a thermostat, and through the tube a mixture consisting of 111 g of propionic acid, 86 g of vinyl acetate, 12.25 g of potassium acetate, 83.7 mg of copper(II) bromide and 158.8 mg of copper(II) acetate was passed continuously at a rate of 40 g/hour. As a result, a liquid flowing out of the tube was analyzed by means of gas chromatography, to find that 49% of the vinyl acetate in the feed was converted into vinyl propionate.

It was found that the catalyst exhibited unchanged activities even after 200 hours of continued reaction carried out under the same conditions.

EXAMPLE 13

The same experimental procedure as in Example 9 was repeated except that 72 g of acrylic acid was employed as the starting carboxylic acid instead of propionic acid. The yield of vinyl acrylate was 39.2 g with 24.0 g of acetic acid recovered as the byproduct.

EXAMPLE 14

A solution consisting of 4.88 g of benzoic acid, 24.8 of vinyl acetate, 0.4 g of potassium acetate, 89.4 mg of copper(II) bromide and 20 ml of tetrahydrofuran was mixed with 1.34 g of the solid catalyst prepared in Example 9. The resulting mixture was heated at 70° C. for 24 hours in the same manner as in Example 9, to form 4.80 g of vinyl benzoate and recover 1.94 g of acetic acid as the byproduct.

EXAMPLE 15

Granular active carbon of 16 to 32-mesh particle size weighing 7.5 g was placed in a solution of 84 mg of palladium acetate in 10 ml of acetic acid, and allowed to stand overnight at room temperature. Thereupon, the material was filtered and dried at room temperature in a vacuum desiccator, about 57% of palladium acetate having been adsorbed on the active carbon.

The thus obtained palladium-bearing active carbon was dipped in 10 ml of an aqueous solution containing 403 mg of potassium bromide and 154 mg of copper(II) acetate, followed by evaporation of water and drying with heat, to form a solid catalyst.

Into a U-shaped tube of 8 mm in inside diameter which had been filled with 15 ml of the above solid catalyst and kept at 60° C. in a thermostat was passed a mixture consisting of 111 g of propionic acid, 86 g of vinyl acetate, 1.96 g of potassium acetate, 54.5 mg of copper(II) acetate and 23.8 mg of potassium bromide continuously at a flow rate of 37 g/hour. As a result, the liquids flowing out of the tube were periodically analyzed by means of gas chromatography, to find that the conversion of the starting vinyl acetate (hereinafter referred to as the ester conversion) was 43.0% after 10 hours and 41.5% after 100 hours from the beginning of the reaction.

Along with the above gas chromatographic analysis, the out-flowing liquids were analyzed by atomic absorption spectral analysis, to observe the palladium content eluded out. The total amount of palladium contained in the outflowing reaction mixture and determined after 20 hours from the beginning of the reaction was 0.9% of the palladium originally contained in the solid catalyst (hereinafter referred to as the palladium loss).

In comparison, the same experimental procedure as above was repeated, using a solid catalyst prepared in the same manner as above but omitting potassium bromide and copper(II) acetate.

The value of the ester conversion was 8.0% after the first 10 hours of the reaction and 22.7% after the first 100 hours of the same reaction while the palladium loss after the first 20 hours was 38.5%.

EXAMPLE 16

The effluent reaction liquid obtained in Example 15 was subjected to distillation to remove acetic acid and fractions having a lower boiling point than acetic acid. The resulting liquid was mixed with fresh portions of propionic acid and vinyl acetate to form the same composition of mixture as in the feed solution in Example 15. Using this mixture, a reaction was carried out in the same manner as in Example 15. The ester conversion was 42.5% after 10 hours of reaction and 41.7% after 100 hours. The palladium loss after the first 20 hours of reaction was 0.8%.

EXAMPLE 17

Granular active carbon of 16 to 32-mesh particle size weighing 10 g was placed in a solution of 220 mg of palladium chloride in 50 ml of 1 N hydrochloric acid, and allowed to stand at 40° C. for 12 hours.

Thereupon, the material was filtered and dried in a vacuum desiccator. About 99% of the palladium chloride was found adsorbed on the active carbon.

The thus obtained palladium-bearing active carbon was further dipped in 10 ml of an aqueous solution containing 580 mg of potassium bromide, followed by complete evaporation of water content to form a solid catalyst.

Using the above prepared solid catalyst, the same experimental procedure as in Example 15 was carried out. As a result, the ester conversion was 44.0% after 10 hours of reaction and 41.0% after 100 hours and the palladium loss in 20 hours was 0.8%.

In comparison, the same experimental procedure was repeated except the adsorption of potassium bromide was omitted, to give the values of the ester conversion after 10 and 100 hours of reaction were equal to 57.5% and 17.5%, respectively, and the palladium loss in 20 hours was equal to 46.7%.

EXAMPLE 18

The active carbon bearing palladium chloride prepared in the same manner as in Example 17 was placed in an aqueous solution which had been prepared with 3 g of of potassium hydroxide, 10 ml of 37% formalin and 30 ml of distilled water, and allowed to stand overnight at room temperature to reduce the palladium chloride into metallic. Thereupon the material was dipped in 10 ml of an aqueous solution containing 272.5 mg of copper(II) bromide, to prepare a solid catalyst.

Using the above-prepared solid catalyst, the same reaction procedure as in Example 15 was carried out. As a result, the values of the ester conversion after 10 and 100 hours of reaction were equal to 53.0% and 42.7%, respectively, and the palladium loss in 20 hours was equal to 0.8%.

EXAMPLE 19

Granular active carbon of 16 to 32-mesh particle size weighing 10 g was placed in a solution of 350 mg of palladium bromide in 50 ml of 1 N hydrochloric acid, and allowed to stand at 40° C. for 12 hours. Thereupon the material was filtered and dried in a vacuum desiccator. About 99% of the palladium bromide was found adsorbed on the active carbon.

Into a U-shaped tube 8 mm in inner diameter which had been filled with 15 ml of a solid catalyst obtained from the above procedure and kept at 60° C. in a thermostat was passed a reaction mixture prepared with 111 g of propionic acid, 86 g of vinyl acetate, 1.96 g of potassium acetate, 54.5 mg of copper(II) acetate and 23.8 mg of potassium bromide continuously at a flow rate of 35 g/hour. As a result, the values of the ester conversion after 10 and 100 hours of reaction were 53.0% and 44.5%, respectively, and the palladium loss in 20 hours was 0.8%.

EXAMPLES 20-23

Into the same flask as used in Example 1 were introduced 36 g of acrylic acid, 43 g of vinyl acetate, 44.8 mg of palladium acetate, 4.9 g of potassium acetate, and 48.5 mg of copper(II) acetate together with or without a potassium halide as indicated in Table I. The mixture was heated at 60° C. for 6 hours with agitation to ensure good contact of its surface with air.

Precipitation of palladium was witnessed in the mixtures at the end of the reaction time in all examples except Example 21 in which the reaction mixture remained transparent in green.

The yield of the objective vinyl acrylate in each reaction mixture is given in the table, showing a remarkable advantage obtained by the use of potassium bromide.

TABLE I

| Example No. | Potassium halide (amount) | Yield |
|---|---|---|
| 20 | None | 4.9 g |
| 21 | Potassium bromide (59.5 mg) | 20.6 g |
| 22 | Potassium chloride (37.3 mg) | 7.4 g |
| 23 | Potassium iodide (83.0 mg) | 3.0 g |

EXAMPLE 24

This is a comparative example.

A mixture composed of 100 g of stearic acid and 186 g of vinyl acetate was boiled under reflux for 3.5 hours in the presence of 22 mg of a double chloride of palladium and lithium PdCl$_2$.LiCl, having a molar concentration of palladium that was approximately the same as 11.2 mg of palladium acetate used in the reaction mixture in Example 7. After the above reaction time, the mixture was added 30 g of active carbon and shaken for 2 hours at 30° to 35° C., then filtered and fractionally distilled. As a result, only 2.7 g of the desired vinyl stearate was produced.

Even with an extension of the reflux time up to 72 hours, no marked improvement was obtained in the yield of the desired vinyl acetate. This is presumably due to the deactivation of the palladium catalyst by its reduction to the metallic state.

What is claimed is:

1. A method for the preparation of an alkenyl ester of a carboxylic acid represented by the general formula $$R^1COOR^3$$

wherein $R^1$ is a hydrogen atom or a substituted or unsubstituted aliphatic or aromatic monovalent hydrocarbon group and $R^3$ is an alkenyl group, which comprises: subjecting a carboxylic acid represented by the general formula $$R^1COOH$$

wherein $R^1$ is the same as defined above to transesterification reaction in the liquid phase with an ester compound represented by the general formula $$R_2COOR^3$$

wherein $R^2$ is a hydrogen atom or a substituted or unsubstituted monovalent hydrocarbon group which is different from $R^1$ above and $R^3$ is the same as defined above; carrying out said transesterification reaction in the presence of a binary catalyst system comprising a main catalyst of a palladium compound in an amount from about 0.001 to about 0.5 parts by weight remaining as adsorbed on a solid catalyst carrier and a co-catalyst consisting of a combination of an alkali metal compound in an amount from about 1 to about 15 parts by weight and a copper (II) compound in amount from about 0.001 to about 1.0 part by weight, all per 100 parts by weight of the total amount of said carboxylic acid and said ester compound, the weight ratio of said copper (II) compound to said alkali metal compound being in the range from about 0.001 to about 0.5; from about 0.001 to about 0.5 parts by weight of said alkali metal compound being an alkali metal bromide, and from about 0.001 to about 0.5 parts by weight of said copper (II) compound being copper (II) bromide.

2. A method as claimed in claim 1, wherein said alkali metal compound consists of said alkali metal bromide plus an alkali metal compound which is more soluble in said carboxylic acid and ester compound than said alkali metal bromide.

3. The method as claimed in claim 1 wherein said palladium compound and said cocatalyst remain adsorbed on a solid catalyst carrier.

4. The method as claimed in claim 1 wherein said transesterification reaction is carried out in an atmosphere of oxygen or an oxygen-containing gas.

* * * * *